United States Patent
Arora

(10) Patent No.: US 10,418,133 B2
(45) Date of Patent: Sep. 17, 2019

(54) SYSTEM AND METHOD FOR MONITORING CONTAINMENT OF AN EPIDEMIC

(71) Applicant: MasterCard International Incorporated, Purchase, NY (US)

(72) Inventor: Ankur Arora, New Delhi (IN)

(73) Assignee: MASTERCARD INTERNATIONAL INCORPORATED, Purchase, NY (US)

( * ) Notice: Subject to any disclaimer, the term of this patent is extended or adjusted under 35 U.S.C. 154(b) by 818 days.

(21) Appl. No.: 14/960,616

(22) Filed: Dec. 7, 2015

(65) Prior Publication Data
US 2017/0161465 A1 Jun. 8, 2017

(51) Int. Cl.
*G16H 50/80* (2018.01)
*G06Q 30/02* (2012.01)
*G06Q 50/22* (2018.01)

(52) U.S. Cl.
CPC .......... *G16H 50/80* (2018.01); *G06Q 30/0205* (2013.01); *G06Q 50/22* (2013.01)

(58) Field of Classification Search
CPC ...... G06Q 20/04; G06Q 30/02; G06Q 10/109; G06Q 30/0205
See application file for complete search history.

(56) References Cited

U.S. PATENT DOCUMENTS

| | | | |
|---|---|---|---|
| 6,766,277 B2 † | 7/2004 | Siegel | |
| 7,069,233 B2 † | 6/2006 | Bracken | |
| 7,249,006 B2 † | 7/2007 | Lombardo | |
| 2001/0015375 A1* | 8/2001 | Swartz | G06Q 30/06 235/383 |
| 2007/0250468 A1* | 10/2007 | Pieper | G06F 16/958 |
| 2009/0138445 A1* | 5/2009 | White | G06Q 30/02 |
| 2011/0295899 A1* | 12/2011 | James | H04L 67/306 707/784 |
| 2012/0080517 A1* | 4/2012 | Braunstein | G06Q 10/087 235/379 |

(Continued)

OTHER PUBLICATIONS

U.S. Appl. No. 14/546,634, filed Nov. 18, 2014.
U.S. Appl. No. 14/716,253, filed May 19, 2015.

*Primary Examiner* — Reginald R Reyes
(74) *Attorney, Agent, or Firm* — Leason Ellis LLP

(57) ABSTRACT

A system and method is disclosed for monitoring the containment of an epidemic in relation to a location-based restriction using an anonymized database of spending records. The system measures the effectiveness of a restriction by analyzing the spending records of individuals in the population and identifies transaction trends that relate to the restriction and correlates them to the effectiveness of the restriction. Based on the identified transaction trends, the system calculates the effectiveness and analyzes the restrictions according to expected trends and models of epidemic spread by geography. The system utilizes the measured effectiveness and predictive analysis to generate notifications if the effectiveness does not meet prescribed requirements and to recommend corrective action. In addition, the system can dynamically update restrictions, implement new restrictions and in certain embodiments, the system can elicit (and respond to) actions that are taken at remote devices, such as mobile phones, computers and POS terminals.

26 Claims, 5 Drawing Sheets

(56) References Cited

U.S. PATENT DOCUMENTS

| | | | |
|---|---|---|---|
| 2012/0190386 A1* | 7/2012 | Anderson | G01C 15/04 |
| | | | 455/456.3 |
| 2016/0012465 A1* | 1/2016 | Sharp | G06Q 20/18 |
| | | | 705/14.17 |
| 2016/0140311 A1 | 5/2016 | Pastore et al. | |
| 2016/0342770 A1 | 11/2016 | Unser et al. | |

\* cited by examiner
† cited by third party

SYSTEM AND METHOD FOR MONITORING CONTAINMENT OF AN EPIDEMIC

TECHNICAL FIELD OF THE DISCLOSURE

This patent application relates generally to the field of monitoring disease outbreaks, and more particularly to detecting and monitoring containment of an epidemic in relation to a location-based restriction using spending records.

BACKGROUND OF THE DISCLOSURE

Disease surveillance is a practice by which the spread of disease is monitored in order to predict, observe, and minimize the harm caused by outbreak, epidemic, and pandemic situations. In order to slow down the spread of the disease, location-based restrictions can be implemented that are aimed at limiting the movement of citizens around a geographic location. For instance, restrictions can include forced closures of large and popular public spaces such as airports, universities and market places where people come in contact with each other and the risk of disease transmission is higher.

It is difficult to monitor and understand human mobility and activity during an epidemic. Such efforts commonly require human monitoring, which can be costly. Moreover, the information gathered from human monitoring is often incomplete and not detailed enough to understand nuances of human mobility and behavior. For example, human observation of a restricted location during the restriction might provide some insight as to how many people are moving through the location. However, this high-level and limited sample of information can be incomplete and is ultimately not detailed enough to develop a meaningful understanding of the actual movements and habits of the relevant subsets of individuals in the population in response to the restriction. This lack of meaningful data makes it difficult to preemptively warn individuals in high risk areas, or take preventative measures such as implementing additional restrictions, especially when the infection is a rapidly spreading through the population. Thus, it can be appreciated that current methods for disease surveillance present challenges to identifying effective locations for implementing location-based restrictions on mobility and, once a restriction is in place, evaluating how effective the restrictions are at containing the disease spread (e.g., pandemic/epidemic).

Accordingly, it is desirable for a system and method for accurately identifying suitable locations for imposing a location-based restriction to aid in the containment of an epidemic. It is also desirable for a system and method that can more accurately evaluate the human response to imposed location-based restrictions and quantify the efficacy of the restriction on containment without reliance on individuals to actively gather the information. Furthermore, it is desirable for a system that can detect and monitor the containment of an epidemic in real time or near-real time from an anonymized database of spending records. It should be apparent that, depending on applicable laws and regulations, a consumer can opt in, thereby consenting to the use of their payment records as well as any other personal information he or she provides to the systems for monitoring the containment of an epidemic.

It is with respect to these and other considerations that the disclosure made herein is presented.

SUMMARY OF THE DISCLOSURE

According to a first aspect, a computer implemented method is provided for monitoring the containment of an epidemic in relation to a location-based restriction using an anonymized database of spending records. The spending records concern purchases by respective individuals in a population at respective locations and at respective times. In addition, the database of spending records is updated in real time as the individuals conduct additional purchases. The method includes the step of receiving restriction data identifying a restricted location and a timeframe for the restriction and accessing, with a processor from the database of spending records, prior spending records that concern purchases conducted prior to the timeframe and current spending records that concern purchases conducted during the timeframe. The method also includes the step of determining, from the prior spending records, a historical transaction volume relating to the restricted location and determining, from the current spending records, a current transaction volume relating to the restricted location. In addition, the method includes the step of analyzing the current transaction volume relative to the historical transaction volume and computing an effectiveness measure for the restriction based on the analysis. In addition, the method includes the step of transmitting a notification representing the computed effectiveness measure over a network to a remote computing device, wherein the notification is selectively transmitted as a function of the effectiveness measure.

According to another aspect, a system is provided for monitoring the containment of an epidemic in relation to a location-based restriction using an anonymized database of spending records. The spending records concern purchases by respective individuals in a population at respective locations and at respective times, and the database of spending records is updated in real time as the individuals conduct additional purchases. The system includes a non-transitory computer-readable storage medium, a processor configured by executing one or more software modules that include instructions in the form of code and are stored in the storage medium. In particular, the modules include a database module that configures the processor to access, from the database of spending records, prior spending records and current spending records. Prior spending records concern purchases relating to the restricted location and conducted prior to a timeframe of the location-based restriction. The current spending records concern purchases relating to the restricted location and conducted during the timeframe. The software modules also include an analysis module that configures the processor to determine a historical transaction volume relating to the restricted location from the prior spending records and a current transaction volume relating to the restriction from the current spending records. The analysis module also configures the processor to identify one or more transaction volume trends based on the current transaction volume and the historical transaction volume and to compute an effectiveness measure for the restriction based on the identified one or more transaction volume trends. The software modules also include a reporting module that configures the processor to generate a notification representing the computed effectiveness measure and selectively transmit the notification to a remote computing device over a network as a function of the effectiveness measure.

These and other aspects, features, and advantages can be appreciated from the accompanying description of certain embodiments of the disclosure and the accompanying drawing figures and claims.

DETAILED DESCRIPTION OF CERTAIN EMBODIMENTS OF THE DISCLOSURE

Figure 1:
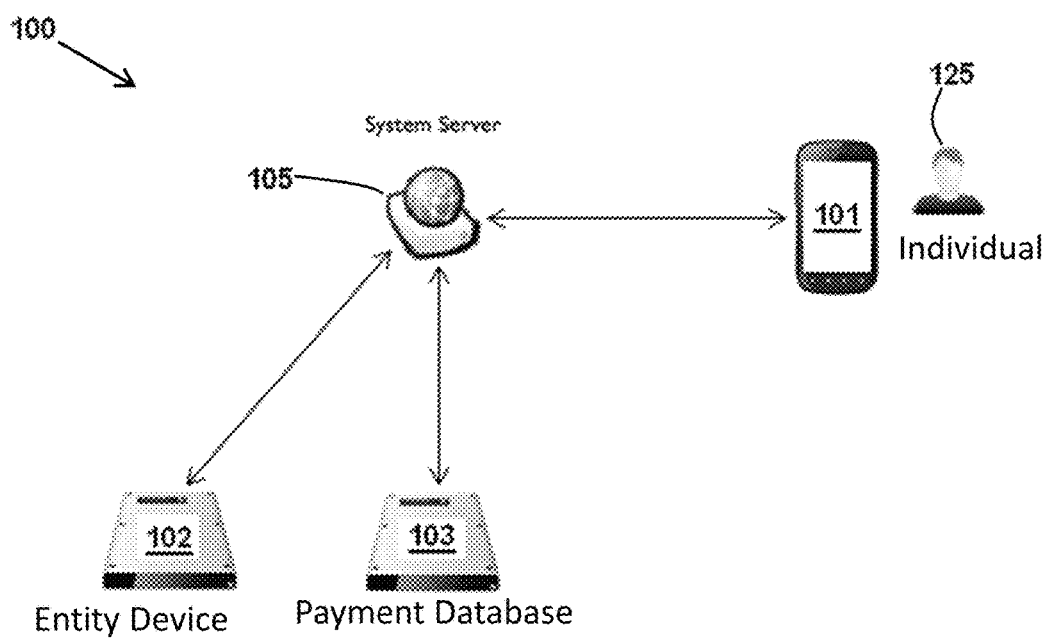
FIG. 1 is a high-level diagram illustrating an exemplary configuration of a system for monitoring the containment of an epidemic in relation to a location-based restriction in accordance with at least one embodiment disclosed herein.

By way of overview and introduction, various systems and methods are described herein that facilitate and enable the real-time monitoring of the containment of an epidemic. The systems and methods have the end goal of identifying effective locations for restricting human mobility and, once in place, monitoring the movement and habits of a population of people to monitor the containment of an epidemic and evaluate the effectiveness of the location-based restriction. The system can achieve this through identifying a historical transaction volume relating to a restricted location, or a location that is a candidate for restriction. Once the historical volume is determined in relation to a location, purchasing data, as it is collected in real time, can be evaluated to monitor the human activity in response to an imposed restriction.

Ultimately the system can compute an effectiveness measure for the restriction based on a comparison of the current and historical transaction data. If the measure exceeds a threshold, the system can generate an alert that is transmitted to individuals in the population and/or to disease control organizations/authorities. For instance, the notification can indicate that the restriction is working to contain the epidemic or advise if additional preventative measures are required to contain the epidemic at the restricted location. Similarly the notification can identify other locations that should be restricted. In addition, the analysis of the human activity can be used to provide notifications directly to certain individuals within the population to advise of risks relating to the epidemic and suggest lower-risk locations that are suitable alternatives to the restricted location.

The following detailed description is directed to systems and methods for monitoring the containment of an epidemic in relation to a location-based restriction. The referenced systems and methods are now described more fully with reference to the accompanying drawings, in which one or more illustrated embodiments and/or arrangements of the systems and methods are shown. The systems and methods are not limited in any way to the illustrated embodiments and/or arrangements as the illustrated embodiments and/or arrangements described below are merely exemplary of the systems and methods, which can be embodied in various forms, as appreciated by one skilled in the art. Therefore, it is to be understood that any structural and functional details disclosed herein are not to be interpreted as limiting the systems and methods, but rather, are provided as a representative embodiment and/or arrangement for teaching one skilled in the art one or more ways to implement the systems and methods. Accordingly, aspects of the present systems and methods can take the form of an entirely hardware embodiment, an entirely software embodiment (including firmware, resident software, micro-code, etc.), or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer. Furthermore, the terms and phrases used herein are not intended to be limiting, but rather, are to provide an understandable description of the systems and methods.

An exemplary system is shown as a block diagram in FIG. 1 which is a high-level diagram illustrating an exemplary configuration of the system for monitoring the containment of an epidemic in relation to a location-based restriction 100. In one arrangement, the system 100 consists of a system server 105 communicatively coupled to at least one payment database 103 (also referred to herein as "spending records" database) and one or more remote computing devices. The remote computing devices (e.g., individual device 101 and entity device 102) can be associated with individuals (e.g., individual 125) from among the population and/or other medical and regulatory entities, such as the U.S. Centers for Disease Control and Prevention (CDC).

The system server 105 can be practically any computing device and/or data processing apparatus capable of communicating with remote computing devices, data storage devices and computing networks (e.g., individual device 101, entity device 102, payment database 103, and the like), receiving, transmitting and storing electronic information and processing information as further described herein. Similarly, payment database 103 is intended to represent various forms of digital computers, such as laptops, desktops, workstations, servers, blade servers, mainframes, and other appropriate computers and/or networked or cloud based computing systems.

Remote computing devices, e.g., individual device 101 and entity device 102, can be configured to collect (and/or display) information from one or more individuals in the population and entities, communicate the information to the system server 105 and receive information from the system server. It should be understood that remote computing devices can be any computing device and/or data processing apparatus capable of embodying the systems and/or methods described herein, including, but not limited to, a personal computer, tablet computer or smart phone device.

Embodiments of the methods and systems described herein, in particular, the payment database 103, can be associated with a payment processing subsystem that is configured to record and/or process spending records detailing purchase transactions conducted by consumers (e.g., individual 125) and one or more merchants or service providers. For example and without limitation, payment database 103 can be associated with a payment card network operated by MasterCard International Incorporated of Purchase N.Y., the assignee of the present disclosure.

Accordingly, payment database 103 can store information spending records concerning purchase transactions performed by individuals in the population with merchants using a transaction card. As used herein, the terms "transaction card," "financial transaction card," and "payment card" refer to any suitable transaction card, such as a credit card, a debit card, a prepaid card, a charge card, a membership card, a promotional card, a frequent flyer card, an identification card, a prepaid card, a gift card, and/or any other device that may hold payment account information, such as mobile phones, smartphones, personal digital assistants (PDAs), digital wallets, key fobs, and/or computers and cloud-based payment schemes. Each type of transaction card can be used as a method of payment for performing a transaction. As would be understood by those skilled in the art, after a purchase has been made using a transaction card, a clearing process occurs to transfer additional transaction data related to the purchase among the parties to the transaction, such as a merchant bank, an interchange network, and issuer bank. More specifically, during and/or after the clearing process, SKU-level data, such as a time of purchase, geographic location of purchase, and purchase data including: a merchant name, a type of merchant, cardholder account information, a type of transaction, information regarding the purchased item and/or service, and/or other suitable information associated with a transaction can be transmitted between parties to the transaction and may be stored by any of the parties to the transaction, for example, in payment database 103.

Figure 2:
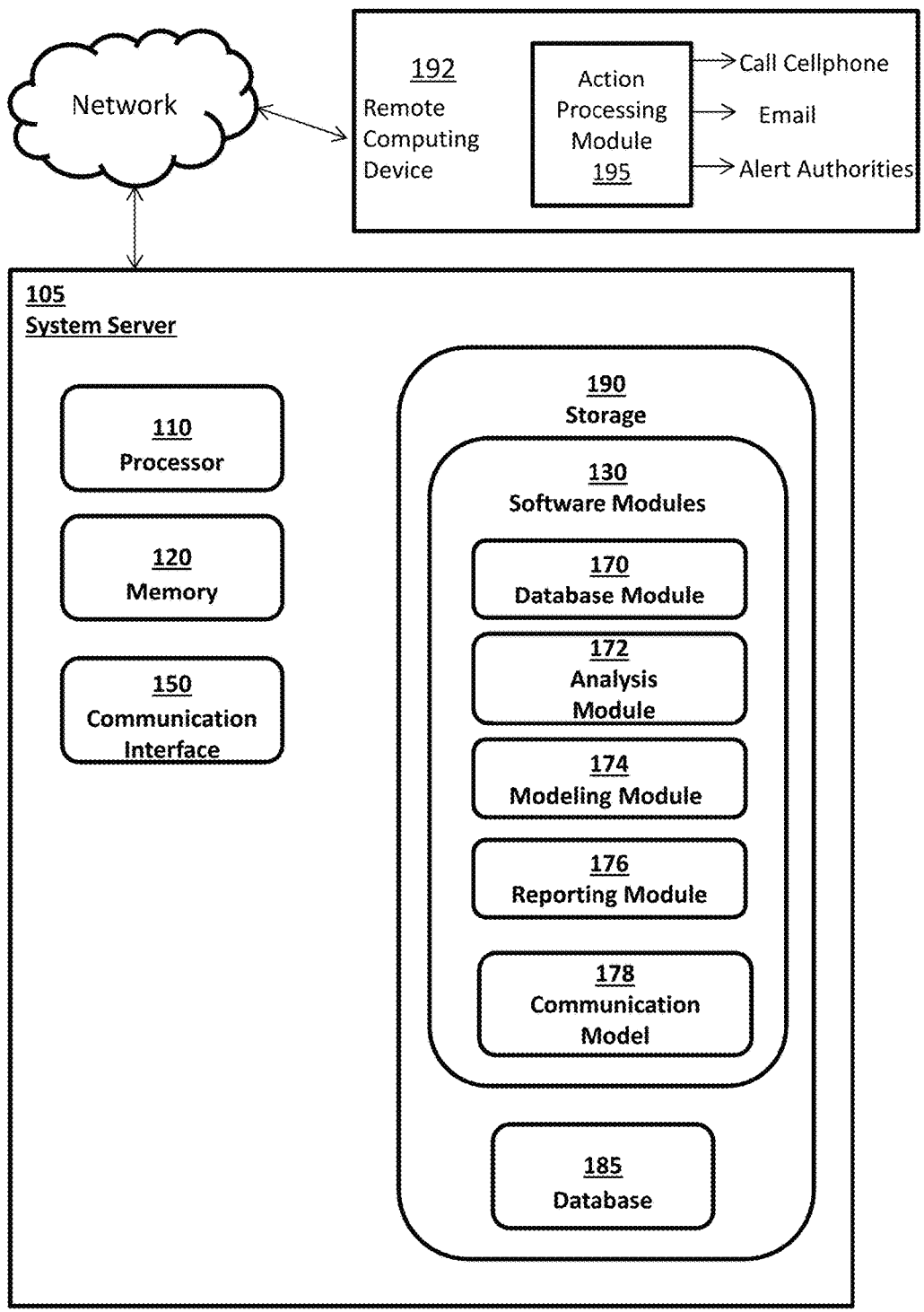
FIG. 2 is a block diagram illustrating an exemplary configuration of a system for monitoring the containment of an epidemic in accordance with at least one embodiment disclosed herein.

In reference to FIG. 2, system server 105 of the system for conducting real-time active surveillance of disease outbreak 100 is arranged with various hardware and software components that serve to enable operation of the system, including a processor 110, a memory 120, a storage 190 and a communication interface 150. The processor 110 serves to execute software instructions that can be loaded into the memory 120. The processor 110 can be a number of processors, a multi-processor core, or some other type of processor, depending on the particular implementation.

Preferably, the memory 120 and/or the storage 190 are accessible by the processor 110, thereby enabling the processor 110 to receive and execute instructions stored on the memory 120 and/or on the storage 190. The memory 120 can be, for example, a random access memory (RAM) or any other suitable volatile or non-volatile computer readable storage medium. In addition, the memory 120 can be fixed or removable. The storage 190 can take various forms, depending on the particular implementation. For example, the storage 190 can contain one or more components or devices such as a hard drive, a flash memory, a rewritable optical disk, a rewritable magnetic tape, or some combination of the above. The storage 190 also can be fixed or removable or remote such as cloud based data storage systems.

The one or more software modules 130 are encoded in the storage 190 and/or in the memory 120. The software modules 130 can comprise one or more software programs or applications having computer program code or a set of instructions executed in the processor 110. Such computer program code or instructions for carrying out operations for aspects of the systems and methods disclosed herein can be written in any combination of one or more programming languages. The program code can execute entirely on system server 105, partly on system server 105, as a stand-alone software package, partly on system server 105 and partly on a remote computer/device such as individual device 101, entity device 102, or any computing devices maintaining the payment database 103 or entirely on the remote computers/devices. In the latter scenario, the remote computer systems can be connected to system server 105 through any type of network, including a local area network (LAN) or a wide area network (WAN), or the connection can be made to an external computer (for example, through the Internet using an Internet Service Provider).

Preferably, included among the software modules 130 is a database module 170, an analysis module 172, a modeling module 174, a reporting module 176 and a communication module 178, that are executed by processor 110. During execution of the software modules 130, the processor 110 is configured to perform various operations relating to the real-time monitoring of the containment of an epidemic in relation to a location-based restriction, as will be described in greater detail below.

It can also be said that the program code of the software modules 130 and one or more of the non-transitory computer readable storage devices (such as the memory 120 and/or the storage 190) form a computer program product that can be manufactured and/or distributed in accordance with the present disclosure, as is known to those of ordinary skill in the art.

It should be understood that in some illustrative embodiments, one or more of the software modules 130 can be downloaded over a network to the storage 190 from another device or system via communication interface 150 for use within the system for conducting real-time active surveillance of disease outbreak 100. In addition, it should be noted that other information and/or data relevant to the operation of the present systems and methods can also be stored on the storage 190, as will be discussed in greater detail below.

A database 185 can also be stored on the storage 190. Database 185 can contain and/or maintain various data items and elements that are utilized throughout the various operations of the system for monitoring the containment of an epidemic in relation to a location-based restriction 100. The information stored in database 185 can include, but is not limited to, information relating to one or more epidemic related location restrictions, spending records, and demographic data relating to the individuals in the population, as will be described in greater detail herein. It should be noted that although database 185 is depicted as being configured locally to system server 105, in certain implementations, database 185 and/or various of the data elements stored therein can be located remotely (such as on a remote device or server—not shown) and connected to system server 105 through a network in a manner known to those of ordinary skill in the art.

A communication interface 150 is also operatively connected to the processor 110 and can be any interface that enables communication between the system server 105 and external devices, machines and/or elements. Preferably, the communication interface 150 includes, but is not limited to, a modem, a Network Interface Card (NIC), an integrated network interface, a radio frequency transmitter/receiver (e.g., Bluetooth, cellular, NFC), a satellite communication transmitter/receiver, an infrared port, a USB connection, and/or any other such interfaces for connecting system server 105 to other computing devices and/or communication networks, such as private networks and the Internet. Such connections can include a wired connection or a wireless connection (e.g., using the IEEE 802.11 standard) though it should be understood that communication interface 150 can be practically any interface that enables communication to/from the system server 105.

It should be understood that any of the computing devices 101, 102, and 103 can be in direct communication with system server 105, indirect communication with system server 105, and/or can be communicatively coordinated with system server 105 through a computer network such as the Internet.

The operation of the system monitoring the containment of an epidemic in relation to a location-based restriction 100 and the various elements and components described above will be further appreciated with reference to the method for monitoring the containment of an epidemic in relation to a location-based restriction as described below, in conjunction with FIG. 3.

At some point prior to monitoring the containment of an epidemic in relation to a location-based restriction in accordance with at least one embodiment disclosed herein, one or more of the individuals in the population can be enrolled to participate in the program for monitoring the containment of an epidemic in relation to a location-based restriction implemented by the system. For example, this can be done by connecting to system server 105 using a consumer device 101 and actively providing personal information, such as, payment account information and the like. It should be understood that, alternatively, the individuals can simply opt in by providing a few key pieces of personal information, such as a name and/or social security number, and grant permission for the system server 105 to access his or her spending records and/or demographic data from the appropriate data storage devices (e.g., payment database 103). In addition, the particular consumer's information could be automatically available to the system by virtue of having a payment card issued by a participating card issuer. Using either personal information or payment information, system server 105, via a transaction processing company, card issuer, and the like, can automatically retrieve spending records for the particular consumer. Any automatic access to a consumer's spending records or medical information would be subject to applicable data privacy and data usages laws.

It should be understood that spending records can be provided by the consumer or also received directly from a participating service provider company, with the appropriate consents from the consumer. It should also be understood that the consumer can also require authorization before the system server retrieves spending records and personal information. Thus, it should be apparent that in the exemplary system and routine described herein, depending on applicable laws and regulations, a consumer can opt in, thereby consenting to the use of their spending records as well as any other personal information he or she provides.

For situations in which the systems discussed here collect personal information about individuals, the individuals may be provided with an opportunity to control the manner such information is collected with respect to programs or features that may collect personal information (e.g., information about an individual's medical data, spending records or an individual's current location/address). Individuals may also be informed of the accompanying limitations on the functionality of a service that may result from limiting access to such personal information. In addition, certain data may be anonymized in one or more ways before it is stored or used, so that personally identifiable information is removed. For example, identifiers associated with an individual's identity, payment records and the like may be anonymized so that no personally identifiable information can be determined for the individuals.

Figure 3:
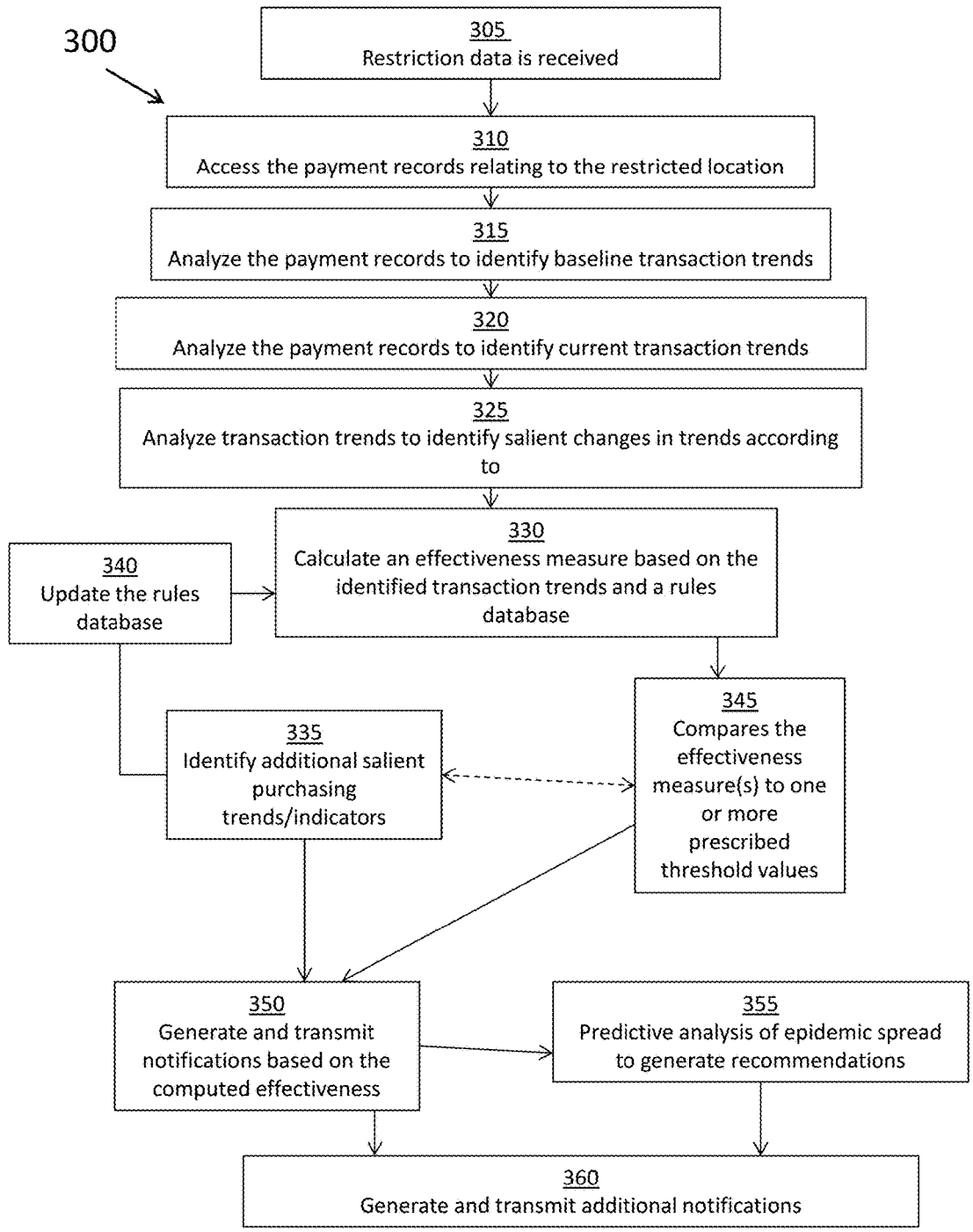
FIG. 3 is a flow diagram illustrating a routine for monitoring the containment of an epidemic in accordance with at least one embodiment disclosed herein.

Turning now to FIG. 3, a flow diagram illustrates a routine 300 for monitoring the containment of an epidemic in relation to a location-based restriction in accordance with at least one embodiment disclosed herein.

The process begins at step 305, in which restriction data is obtained. Restriction data includes information identifying one or more restricted locations and a timeframe for the restriction(s). Restriction data can be generated by the system server 105 by analyzing transaction trends to identify high risk locations that should be subject to a restriction, as further described herein. In addition or alternatively, restriction data can be defined by an outside source, for instance a governmental body that imposes such restrictions, and provided to the system server 105 as an input.

At step 310, the system server 105 accesses the payment records relating to the restricted location. More particularly, by example and without limitation, the processor 110, which is configured by executing one or more of the software modules 130, including, preferably, the database module 170, the analysis module 172, and the communication module 176, can access the payment database 103 to retrieve the spending records that are associated with a particular restriction.

In particular, the configured processor 110 can identify prior spending records that concern purchases conducted prior to the restriction timeframe and relating to the restricted location. The spending records can include, but are not limited to, records of purchases (i.e., transactions) conducted by one or more individuals in the population using a variety of payment methods, such as a credit card, a debit card, a prepaid card, a gift card, bank account bill-pay service, ACH payment, a TSM account, or a combination of the foregoing. The spending records can be retrieved from a data source, such as payment database 103, which can be operated by a payment service provider, such as MasterCard International Incorporated, the assignee of the present disclosure. As previously noted each record can include transaction data, such as a time of purchase, location of purchase, and purchase data including: a merchant name, a type of merchant, cardholder account information, a type of transaction, information regarding the purchased item and/or service, and/or other suitable information associated with the transaction.

In addition to accessing prior spending records relating to the restriction and restricted location, the configured processor can also access current spending records for purchases that were/are conducted during the timeframe of the restriction and that similarly relate to the restricted location. It should be understood that the current spending records can be retrieved periodically while evaluating and monitoring the containment of the epidemic, dynamically while monitoring the containment during the timeframe or a combination of the foregoing. For instance current spending records can be retrieved for a defined time-window that begins with the imposition of the restriction (e.g., a particular week during the restriction). By way of further example, the current spending records can be limited to the immediately preceding 24 hours. In addition, spending records can accessed in near-real time for more dynamic and granular monitoring (e.g., hourly, daily, by the minute and the like) while the restriction is in place.

It can be appreciated that various categories of spending records can be identified as having a relation to the restriction and the restricted location. For instance, spending records for transactions that were conducted at the restricted location can provide insight as to the transaction volume at the particular location over a given period of time. By way of further example, spending records for purchases conducted by individuals who have a billing address (e.g., reside) in proximity to the restricted location, or have a history of conducting one or more transactions at the restricted location can also provide insight as to the habits of individuals in relation to the restricted location. As further described herein, purchase transactions that relate to the restricted location in a variety of different ways can be identified from the database of spending records and analyzed so as to identify trends and algorithmically evaluate the efficacy of the restriction based on the changes in the identified trends prior to, during and/or after a restriction.

At step 315, the system analyzes the payment records relating to the restricted location to identify baseline transaction trends relating to the restricted location prior to the restriction. At step 320, the system analyzes the payment records relating to the restricted location during the time of the restriction. More particularly, by example and without limitation, the processor 110, which is configured by executing one or more of the software modules 130, including, preferably, the database module 170, the analysis module 172, and the communication module 176, in steps 315 and 320, can analyze the current spending records associated with a particular restriction or location to identify the transaction trends relating to the restricted location during the time of restriction and/or thereafter.

At step 325, the configured processor analyzes the transaction trends from before the restriction and the current transaction trends during or after the restriction to identify salient changes in transaction trends and monitor the transaction trends.

Figure 4A:
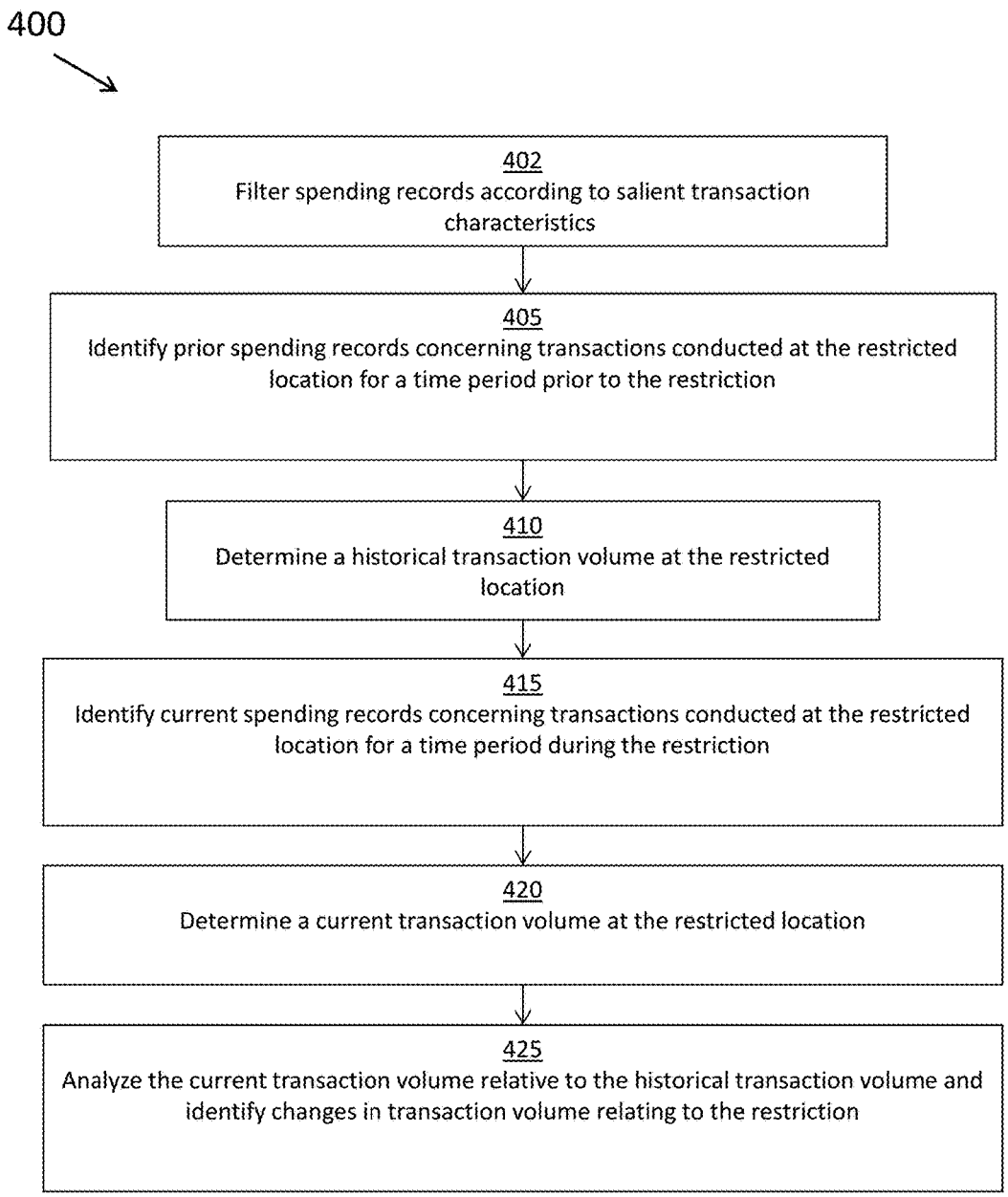
FIG. 4A is a flow diagram illustrating a routine for monitoring transaction trends in accordance with at least one embodiment disclosed herein.
Figure 4B:
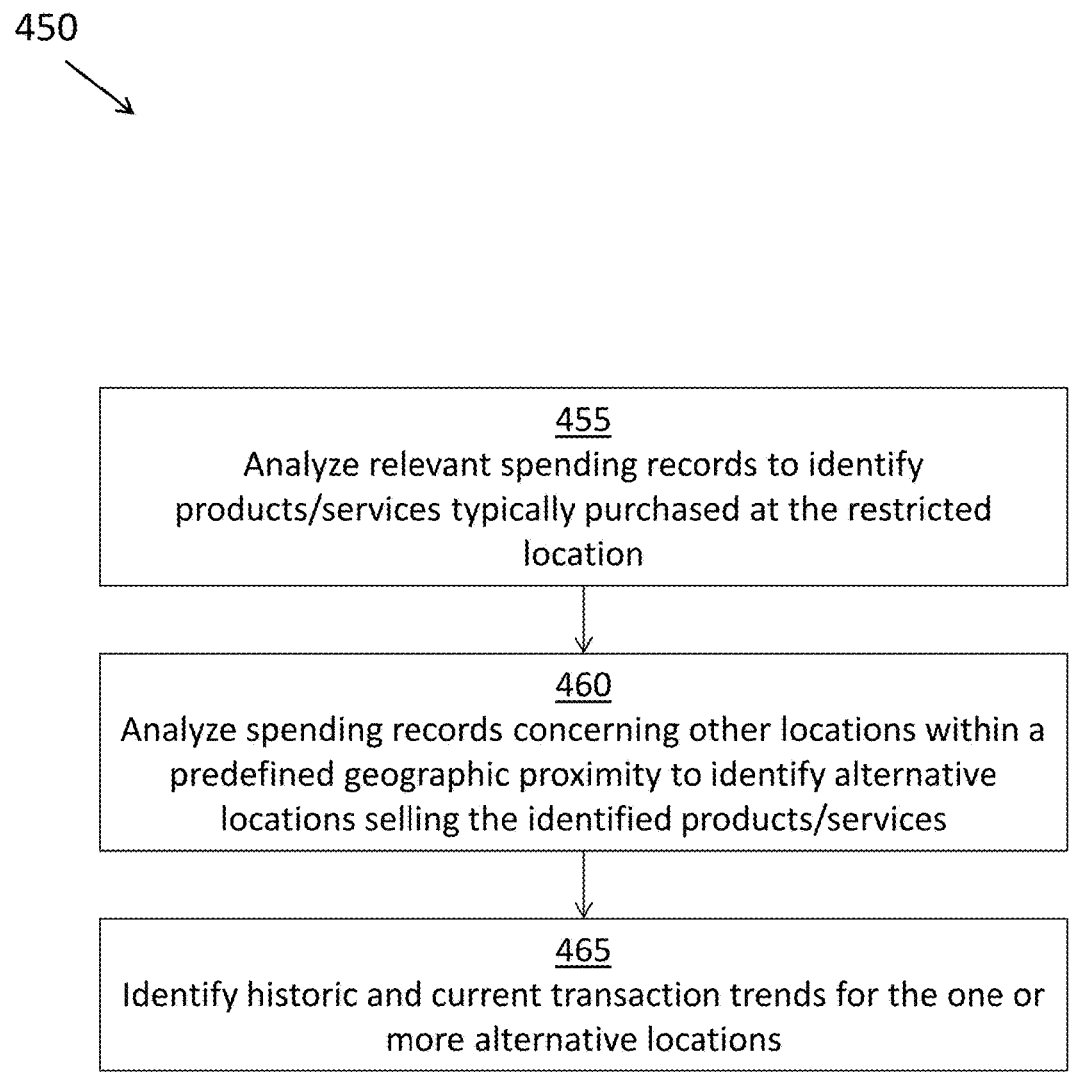
FIG. 4B is a flow diagram illustrating a routine for evaluating the effect of the location-based restriction in accordance with at least one embodiment disclosed herein.

Exemplary methods for identifying relevant spending records and analyzing the spending records to identify salient transaction trends are further described in relation to FIGS. 4A-4B. As noted above, various types of transaction trends can identified from the prior and current spending records and evaluated to determine whether the restriction is effective in containing the epidemic. FIG. 4A depicts an exemplary method 400 for identifying salient transaction trends as a function of the volume of transactions conducted at the restricted location. More specifically, at step 405, the processor 110, which is configured by executing one or more of the software modules 130, including, preferably, the database module 170 and the analysis module 172, can identify from the spending record database 103 the prior spending records that concern transactions conducted at the restricted location (e.g., merchant locations within the geographic area corresponding to the restricted location) within a defined period of time prior to the restriction. Based on the prior spending records, at step 410, the configured processor can determine a historical transaction volume for the restricted location. Similarly, at step 415, the configured processor can identify the current spending records for transactions conducted at the restricted location for one or more periods of time during the restriction and calculate a current transaction volume at the restricted location for the one or more periods, at step 420. Subsequently, at step 425, the configured processor can analyze the current transaction volume relative to the historical transaction volume to measure the change in transaction volume in relation to the restriction. For instance, the configured processor can determine whether trends in transaction volume represent a reduction in transaction volume thereby indicating that the individuals in the population are complying with the restriction.

A targeted analysis of spending records can be beneficial in minimizing the possibility that the identified transaction trends are skewed by factors that are unrelated to the restriction. Accordingly the exemplary routine 400 can start with one or more filtering steps, i.e., step 402, such that a relevant subset of spending records having certain salient characteristics are analyzed to identify transaction trends. For instance transaction trends can be identified for a specific subset of individuals in the population such as, individuals with a billing address in proximity to the restricted location or individuals that have a history of conducting transactions at the restricted location. More specifically, the configured processor 110 can identify, from the database of spending records 103, a subset of relevant individuals in the population that have conducted transactions at the restricted location and also have a billing address that is proximate to the restricted location. The configured processor can then determine, for the subset of individuals, a historical transaction volume at the restricted location prior to the restriction and a current transaction volume at the restricted location for one or more periods of time during the restriction. Accordingly, transaction trends for the relevant set of individuals can be determined as a function of the current transaction volume and the historical transaction volume.

In order to algorithmically develop a more complete understanding as to the behavior of the population of individuals in response to the restriction and thus more accurately evaluate the effect of the restriction, transaction trends relating to the restricted location can be evaluated in view of transaction trends for other locations that are not restricted yet still are possibly affected by the restriction. For instance, trends in transaction volume at the particular restricted location can be compared to changes in transaction volume at one or more other physical locations that are not restricted and that sell similar products/services as the restricted location. By way of further example, trends in online transaction activity for a relevant subset of individuals in the population can also be evaluated.

FIG. 4B depicts an exemplary routine 450 for evaluating the effect of the restriction in view of transactions conducted at alternative location. More specifically, at step 455, the processor 110, which is configured by executing one or more of the software modules 130, including, preferably, the database module 170 and the analysis module 172, can identify from the spending record database 103 the particular types of products/services typically purchased at the restricted location. At step 460, the configured processor 110 can similarly analyze spending records concerning un-restricted locations that are within a predefined geographic proximity (e.g., within a 5 mile radius) of the restricted location to identify suitable alternative locations where the identified products/services are also available. Then at step 465, historic and current transaction trends are identified for the one or more alternative locations, for instance in the manner described in relation to steps 410-425.

In the case of evaluating changes in online purchasing activity, spending records for the subset of individuals living near the restricted location can be similarly analyzed to identify changes in online purchasing volume for the goods/services that are normally available at the restricted location. More specifically, the configured processor 110 can compare the historical volume of transactions conducted by the subset of individuals with online merchants to the current online transaction volume to identify changes in purchasing patterns around the time of the restriction.

Accordingly, it can be appreciated that a comparative analysis of the transaction trends for the restricted location and the alternative locations (e.g., proximate unrestricted locations and/or online merchants) can be performed to determine whether the relevant set of individuals are more frequently conducting transactions at the alternative locations than at the restricted location, which can be an indication that the restriction is being followed by those individuals. As noted above, in some implementations, the comparative analysis of purchase trends can be focused on individuals having a relation to the location and/or based on the types of purchases typically conducted at the restricted location.

It should be understood that the system server 105 can be configured to segment the spending records to be analyzed according to a variety of criteria relating to the individuals in the population, for instance, demographic criteria including, but not limited to, age, address, location, education level, occupation, and family-related data, such as marital status and number of children and the like. Demographic data can be determined by analyzing the spending records retrieved from the payment database 103 or can be obtained from third party providers of such information or from the individuals themselves. Similarly, spending records can be segmented by merchant, product, location and other attributes of the transactions that are recorded in the spending records.

Returning again to FIG. 3, at step 330, an effectiveness measure is calculated based on the identified transaction trends. More specifically, the processor 110, which is configured by executing one or more of the software modules 130, including, preferably, the analysis module 172, can compare the identified transaction trends to expected trends or other prescribed indicators that represent whether a location-based restriction is effective, or not. Various criteria concerning the expected trends and indicators can be provided to and/or identified automatically by the system server 105 and stored as rules in the database 185 for application during the analysis. Expected trends that have been previously stored by the system server can include, for example and without limitation, a decrease in transaction volume at the restricted location during the restriction or an increase in transaction volume in one or more alternative locations.

In some implementations, the effectiveness measure can be calculated as a function of how closely the identified trend compares to an expected trend. For instance, the change in transaction volume over one or more prescribed intervals can be compared to an expected change in transaction volume (e.g., a prescribed value of increase or decrease in transaction volume) to calculate whether the change meets the expected criteria and by how much. By way of further example, in some implementations, the effectiveness measure can be calculated as a function of how sharply the transaction volume changes at one or more points in time before or after the restriction is implemented. For instance, the rate of change in transaction volume during the period after the restriction is implemented can be compared to an expected rate of change and the effectiveness measure can be computed based on the degree to which the rate of change meets, exceeds or falls short of the expected rate of change. The quantitative analysis of transaction trends can be performed using any number of algorithmic and mathematical analysis techniques, as would be understood by those in the art. It can also be appreciated that the different types of transaction trends can be analyzed individually, relative to one-another (e.g., the changes in transaction volume at an alternative location compared to the change in transaction volume at the restricted location over a number of different time periods), collectively or a combination of the foregoing. It can be further appreciated that because some transaction trends can provide a more reliable measure of the effectiveness of a restriction than others, individually computed effectiveness scores can be weighted accordingly and combined to compute an overall effectiveness score.

In addition to comparing identified trends to expected trends and known indicators, it can also be appreciated that trends representing the purchasing behavior of the population (and subsets thereof) can be analyzed, at step 335, to identify trends in consumer purchasing behavior that were previously unknown, show a correlation to the restriction and are thus representative of the effect of the restriction. Accordingly, as shown in feedback step 340, the configured processor can update the set of expected trends and prescribed indicators so as to provide a more complete and dynamically updating set of expected trends and indicators as more data is being analyzed and more transaction trends are determined to relate to the restriction.

Then at step 345, the configured processor 110 compares the effectiveness measure to one or more prescribed threshold values to determine whether the restriction meets or exceeds prescribed requirements for the restriction. Because the effectiveness measure can be computed based on various categories of transaction trends that are considered individually or in combination, respective threshold values can be applied based on the particular manner in which the effectiveness measure was calculated. In addition, in some implementations, the threshold levels can define ranges of values that define degrees of effectiveness such that different actions can be taken depending on the determined degree of effectiveness, as further described herein.

At step 350, the system server transmits one or more notifications or alerts based on the determined effectiveness of the restriction. More specifically, the processor 110, which is configured by executing one or more of the software modules 130, including, preferably, the analysis module 172, can based on the comparison of the effectiveness measure to the threshold(s) generate a report that represents the effectiveness of the restriction. In some implementations, different reports can be generated based on the degree of effectiveness or reports for transmission to a particular receiving entity. For instance, if the restriction is not effective (i.e., an effectiveness measure that is below a low threshold), the notification can indicate the deficiency and can be automatically transmitted to the governmental body that imposed the restriction or is enforcing the restriction.

In another implementation, the notification can provide a more detailed analysis of the effect of the restriction. For instance, the notification can break down the effectiveness according to different segments of the population and provide transaction trends for various categories of transactions, say, transaction trends at the restricted location, the transaction trends for one or more alternative location, and the like. In addition, because the transaction analysis can be performed for surrounding locations, the notification an also include suggestions as to how the restriction can be modified to improve the effectiveness of the restriction.

In some implementations, the real-time transaction volume and transaction trends can be analyzed in view of epidemic spread models, for instance, geographic and temporal epidemic spread models. As would be understood by those skilled in the art, there exist algorithmic models that project how various diseases spread through a population. Because infection with disease is commonly spread through human-human interaction, such geographic infection spread models are used to project the spread of epidemics within a population across a geographic area and over time.

More specifically, at step 355, the processor 110, which is configured by executing one or more of the software modules 130, including, preferably, the analysis module 172 and the modeling module 174 can seed an epidemic spread model with information concerning the real-time or historic transaction volume and trend data relating to the restricted locations and/or the surrounding areas and analyze the model projections. Based on the analysis the configured processor 110 can algorithmically predict the risk of epidemic spread and rate of epidemic spread at various locations (e.g., the restricted location and other un-restricted locations) for current and future time periods and according to a variety of factors relating to epidemic spread.

The configured processor 110 can use the information from the model analysis to define the target thresholds that are used to measure the effectiveness of existing location-based restrictions and to predict the effect that altering the current restriction would have at curbing the spread of an epidemic (e.g., making it smaller or larger in area, shorter or longer in duration or more/less restrictive on human mobility). In addition, the seeded model can be used to identify additional locations that, if restricted, would be effective at curbing epidemic spread based on the current state of the epidemic and transaction trends and, in addition, the processor 110 can define the appropriate thresholds for monitoring effectiveness. It can also be appreciated that the geographic locations identified using the infection spread model as high risk areas can be analyzed with higher scrutiny as compared to lower risk geographic locations to make the overall analysis more efficient and targeted.

Based on the determined restriction effectiveness and/or the predictive analysis of epidemic spread and risk, the configured processor 110 can also be configured to provide additional advisory notifications, at step 360. These notifications can be transmitted automatically based on the relative effectiveness of the restriction or as a supplemental service to help individuals avoid going to the restricted location or other at-risk locations. For instance, in some implementations the configured processor 110 can identify from the database of spending records 103 physical or electronic contact addresses (e.g., SMS number or Email address) for a relevant subset of individuals in at-risk areas and transmit a notification to those individuals. The notifications can provide the name and address of the nearby un-restricted locations that are safer alternatives to the restricted location. Similarly, the notification can provide one or more online sources for the particular goods of interest such that the individuals do not have to go to a physical store location to purchase the goods and avoid unnecessary exposure. In some implementations, the configured processor 110 can generate and transmit the notifications in a coordinated manner that mitigates risk of epidemic exposure by minimizing the number of people that are directed to a particular alternative location. For instance, one subset of individuals can be notified of a first alternative location and another subset can be directed to another alternative location so as to minimize the spread of the epidemic.

The effectiveness notification report can provide individuals, or groups of individuals, medical providers, and authorities other regulatory entities information relating to the epidemic and its containment. For example, the report can notify a specific individual that they are at risk for infection (because they are part of a population or set at high risk) or otherwise provide general information concerning the epidemic and the restriction. Reports can also be transmitted to medical care providers or regulatory bodies to inform these entities as to the status of the epidemic and provide relevant information.

The report can be printed and provided in paper form, for example to a known address of the appropriate individuals and entities. Alternatively or in addition, the report can be transmitted in an electronic format over the internet. The outbreak notification report can be transmitted by the configured processor 110 to individuals at respective remote individual devices 101. In addition or alternatively, the report can be transmitted to medical care providers or regulatory bodies at respective remote entity devices 102.

In addition, the configured processor 110, which is configured by executing one or more of software modules 130, including, preferably, the reporting module 176, can automatically generate recommendations for individuals and entities as a function of the geospatial outbreak detection model in view of the spending records. For example, if certain locations were identified as high risk, the report can identify those high risk locations to avoid and be transmitted to the individuals in that and surrounding areas about nearby locations that are high risk areas.

In addition, in certain embodiments, for example when alerts are generated or the calculated risk of infection exceeds certain levels or individuals are performing transactions at restricted locations, the system can cause actions to be taken at one or more remote computing devices, for example, remote computing device 192 shown in FIG. 2.

It can be appreciated that remote computing device 192 can be configured to coordinate electronic communication over a network between the system server 105 and/or other remote devices (e.g., individual device 101) and stand-alone computers, devices or servers (e.g., entity device 102) and coordinate action across the various remote devices. In some implementations, the remote devices can be transaction processing systems or related devices such as point of sale (POS) terminals at the restricted location. It can also be appreciated that the features and functionality of the remote computing device 192 can be distributed across one or more computing devices, such as the system server 105 and/or mobile devices (e.g., the individual device 101, the entity device 102, POS terminals, and the like). As shown in FIG. 2, the remote computing device 192 preferably includes one or more processors that are configured by executing one or more software modules, including an action processing module 195 that executes so as to configure the remote computing device 192 to perform certain actions in response to transmissions received from the system server 105 over a network.

In some implementations, the system server processor 110, which is configured by executing one or more of software modules 130, including, preferably, the reporting module 176, can transmit an alert over a network to the remote computing device 192, and causing at least one action to be taken at the remote computing device 192 in response to the transmission. In response to receipt of an alert or information relating to infection by one or more individuals conducting one or more purchases from the system server 105, the remote computing device 192, which is configured by executing the action processing module 195, can cause various actions to occur at the remote devices.

In some implementations, the configured remote computing device 192 can cause a telephone call to be placed to a particular individual's mobile device or transmit a message or e-mail to the particular individual or alert the authorities.

In this manner, the computing device can also generate and transmit reports as described above.

In some implementations, the configured remote computing device 192 can be configured to elicit an action from the recipients of the messages. For example, the remote computing device 192 can present a message to the particular individual and prompt that individual to take a certain action, like call a governmental body, or confirm receipt of the message or input additional information.

By way of further example, the remote computing device 192 can cause actions to occur at remote computing devices, for example, the remote computing device 192 can cause a point of sale terminal to notify an individual conducting a purchase of an elevated risk of epidemic exposure at that location or inform the individual of a restriction and alternative locations to go to or medical locations to visit. In addition the remote computing device 192 can cause a remote transaction processing system or POS terminal to decline or delay a purchase being conducted by an individual, for example, if the terminal or the particular purchase transaction is occurring at a restricted or high risk location, or if the individual is determined to have a high likelihood of infection or is known to be infected and the like. In addition the remote computing device 192 can cause the terminal to decline or hold a transaction being conducted by an individual pending an action by the individual at that terminal or another device. For example, the transaction can be delayed pending the individual responding to a message transmitted to their mobile device, or pending the user indicating receipt of a message provided via the terminal.

Accordingly it can be appreciated that the system 100, which includes the system server 105 in conjunction with the remote computing device 192 and remote devices distributed across a network, is configured to analyze and detect disease spread based on payment records that are updated in near-real time, proactively warn the population and authorities in an efficient and effective manner and aid in the efficient prevention of disease via the distributed network of computing devices.

In view of the foregoing, it can be appreciated that the system server 105, which is configured to analyze a continuously updating database of spending records 103 to determine: the effectiveness of location-based restrictions; evaluate human mobility and predict risk-levels associated with various geographic locations in near-real time; identify new restricted locations; automatically assign or update the thresholds that are used to measure effectiveness of restrictions based on a variety of different behavioral characteristics reflected in the spending records; generate automatic notifications that report the effectiveness, suggest modifications to restrictions and/or coordinate the purchasing actions of the relevant individuals in the population; provides an automated and dynamically adjusting system for monitoring epidemic spread in view of location-based restrictions and proactively mitigate risk of epidemic exposure while also providing important information to the population.

In some implementations, the analysis of spending records and the modeling of the epidemic spread can be supplemented with an analysis of the purchasing activity of individuals in the population that are known to be infected by a disease. In particular, spending records, including geographic data, temporal data and purchase data, for example, can be analyzed to identify the locations visited by known infected individuals and to identify physical/temporal intersections of the infected individuals with other individuals in the population (e.g., based on the location/times associated with their respective spending records). Accordingly, the movements of known infected individuals and other individuals in the population that possibly came in contact with an infected individual can be used to monitor epidemic spread and dynamically update a geospatial epidemic spread model as additional spending record data is being collected. In addition, based on identified intersections between infected individuals and other individuals in the population, notifications can be generated and transmitted to the at-risk individuals to advise the individuals of a potential risk.

In some implementations, the analysis of spending records and the dynamic modeling of the epidemic spread can be informed by an analysis of product purchases that have a correlation with the epidemic. More specifically, the configured processor 110 can analyze the information data included in the spending records to identify purchases that are indicative of infection in the population. As noted above, the spending records can include data that identifies one or more of a product, a service, a merchant, a location of purchase, a time of purchase and other such information that describes the purchase transaction. In some implementations, the purchase data can be compared to indicators of infection and a correlation between the purchases and one or more of the indicators can be determined. Indicators of infection are purchase attributes that are known to be associated with infection by the at least one disease. For example, and without limitation, the indicators can range from broad categories (e.g., vitamins or health food stores) to specific products or merchants/service providers (e.g., a particular pharmaceutical product, vitamin, or medical provider) that have been associated with the infection or otherwise relate to infection with the disease.

For example and without limitation, exemplary systems and methods for the surveillance of the spread of disease based on spending records are further described herein and in co-pending and commonly assigned U.S. application Ser. No. 14/546,634, entitled "A SYSTEM AND METHOD FOR CONDUCTING REAL TIME ACTIVE SURVEILLANCE OF DISEASE OUTBREAK" and filed on Nov. 18, 2014, and U.S. application Ser. No. 14/716,253, entitled "METHOD AND SYSTEM FOR INTEGRATING INFECTIOUS DISEASE DATA WITH TRANSACTION DATA" and filed on May 19, 2015, which are each hereby incorporated by reference herein as if set forth in their respective entireties herein.

It should be understood that steps for analyzing spending records, identifying transaction trends, predictive modeling of the epidemic spread, computing the effectiveness of the restriction and updating/implementing restrictions can be broken into sub-routines that can be performed in any suitable order or according to any combination of priorities. It should also be understood that the spending records can be analyzed for any number of past time periods, including without limitation, weekly, monthly, quarterly, yearly, etc. by aggregating the spending records for the given time period prior to analysis. In addition or alternatively the system can monitor the effectiveness in near-real time as spending records is received and stored in the database of spending records 103.

At this juncture, it should be noted that although much of the foregoing description has been directed to systems and methods for monitoring the containment of an epidemic in relation to a location-based restriction, the systems and methods disclosed herein can be similarly deployed and/or implemented in scenarios, situations, and settings far beyond the referenced scenarios.

It should be appreciated that more or fewer operations can be performed than shown in the figures and described. These operations can also be performed in a different order than those described. It is to be understood that like numerals in the drawings represent like elements through the several figures, and that not all components and/or steps described and illustrated with reference to the figures are required for all embodiments or arrangements.

Thus, illustrative embodiments and arrangements of the present systems and methods provide a computer implemented method, computer system, and computer program product for real-time active surveillance of disease outbreak. The flowchart and block diagrams in the figures illustrate the architecture, functionality, and operation of possible implementations of systems, methods and computer program products according to various embodiments and arrangements. In this regard, each block in the flowchart or block diagrams can represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The subject matter described above is provided by way of illustration only and should not be construed as limiting. Various modifications and changes can be made to the subject matter described herein without following the example embodiments and applications illustrated and described, and without departing from the true spirit and scope of the present disclosure, which is set forth in the following claims.

What is claimed is:

1. A computer-implemented method for monitoring the containment of an epidemic in relation to a location-based restriction using an anonymized database of spending records, wherein the spending records concern purchases by respective individuals in a population at respective locations and at respective times, and wherein the database of spending records is updated in real time as the individuals conduct additional purchases, the method comprising:

receiving, with a processor configured by instructions in the form of code executing therein, restriction data identifying a restricted location and a timeframe for the restriction;

accessing, with the configured processor from the database of spending records, prior spending records that concern purchases conducted prior to the timeframe and current spending records that concern purchases conducted during the timeframe;

determining, with the configured processor from the prior spending records, a historical transaction volume relating to the restricted location;

determining, with the configured processor from the current spending records, a current transaction volume relating to the restricted location;

analyzing, with the configured processor, the current transaction volume relative to the historical transaction volume;

computing, with the configured processor, an effectiveness measure for the restriction based on the analysis;

comparing the effectiveness measure to a prescribed target level;

based on the effectiveness measure not meeting the prescribed target level, transmitting, with the configured processor over a network to a remote computing device being used by a particular individual to perform a transaction in an area subject to the location-based restriction, a notification configured to cause the remote computing device to prompt the particular individual to perform at least one action at the remote computing device; and delaying, holding or declining the transaction, by the configured processor, pending receipt of an indication from the remote computing device that the least one action was performed by the particular individual at the remote computing device.

2. The method of claim 1, further comprising:

generating a heat-map using the effectiveness measure for the restricted location, wherein the notification representing the computed effectiveness measure includes the generated heat map or a link to retrieve the generated heat map.

3. The method of claim 1, further comprising:

identifying, with the configured processor from the database of spending records, a subset of individuals in the population having a relation to the restricted location, wherein the relation is one or more of: a history of conducting transactions at the restricted location, and a billing address that is proximate to the restricted location.

4. The method of claim 3, further comprising:

determining, with the processor from the prior spending records and the current spending records, a historical transaction volume at the restricted location for the subset of individuals;

determining, with the processor from the current spending records relating to the subset of individuals, a current transaction volume at the restricted location for the subset of individuals; and wherein the effectiveness measure is computed as a function of the current transaction volume at the restricted location for the subset of individuals relative to the historical transaction volume at the restricted location for the subset of individuals.

5. The method of claim 3, further comprising:
   determining, with the processor from the prior spending records, a historical online transaction volume for the subset of individuals;
   determining, with the processor from the current spending records relating to the subset of individuals, a current online transaction volume for the subset of individuals; and
   wherein the effectiveness measure is computed as a function of the current online transaction volume relative to the historical online transaction volume.

6. The method of claim 5, further comprising:
   identifying, with the processor from the database of spending records, one or more products that have a correlation to the epidemic; and
   wherein the effectiveness measure is computed as a function of the current online transaction volume relative to the historical online transaction volume for the one or more products that have a correlation to the epidemic.

7. The method of claim 1, further comprising:
   identifying, from the prior spending records, one or more types of items purchased at the restricted location; and
   identifying, with the processor from the database of spending records, one or more alternative locations to purchase the one or more types of items, wherein the one or more alternative locations are one or more of: online sources of the one or more types of items, and one or more un-restricted locations that are proximate to the restricted location.

8. The method of claim 7, further comprising:
   generating a notification identifying the one or more unrestricted locations; and
   transmitting the notification to at least a subset of individuals in the population having a relation to the restricted location, wherein the relation is one or more of: a history of purchasing items at the restricted location and a billing address that is proximate to the restricted location.

9. The method of claim 7, further comprising:
   determining, with the configured processor from the prior spending records, a historical payment transaction volume relating to the one or more alternative locations;
   determining, with the configured processor from the current spending records, a current payment transaction volume for the one or more alternative locations; and
   wherein the effectiveness measure is computed as a function of the current transaction volume for the one or more alternative locations relative to the historical online transaction volume for the one or more alternative locations.

10. The method of claim 5, wherein the one or more alternative locations are online merchants, and further comprising:
   comparing, with the configured processor, the historical payment transaction volume relating to the online merchants and the current payment transaction volume relating to the online merchants to determine purchase trends including one or more of:
      a relative increase in online transaction volume for one or more products having a correlation to the epidemic;
      a relative increase in transaction volume at one or more alternative locations;
      an increase in online transaction volume for the particular type of goods is increasing relative to in-store purchases; and
      whether purchases volume of the one or more types of goods are increasing in alternative locations relative to the restricted location.

11. The method of claim 1, further comprising:
   detecting, with the processor in real time from the database of spending records, the transactions being performed at the remote computing device in the area subject to the location-based restriction; and
   wherein the notification is transmitted as a function of the effectiveness measure not meeting the prescribed target level and detecting the transactions being performed at the remote computing device.

12. The method of claim 7, further comprising:
   generating a heat-map using one or more of:
      the effectiveness measure for the restricted location,
      a transaction volume for the restricted location, and
      a transaction volume for the one or more unrestricted locations; and
   wherein the notification representing the computed effectiveness measure includes the generated heat map or a link to retrieve the generated heat map.

13. The method of claim 1, further comprising:
   updating the calculated effectiveness measure, using the configured processor in real time as the individuals conduct additional purchases, by repeating the steps of:
      determining the current transaction volume relating to the restricted location;
      analyzing the current transaction volume relative to the historical transaction volume; and
      computing the effectiveness measure for the restriction based on the analysis.

14. The method of claim 1, further comprising:
   identifying, with the processor, a new restricted location based on the effectiveness measure; and
   transmitting, with the processor over the network to one or more remote computing devices, a notification identifying the new restricted area.

15. The method of claim 1, wherein the step of transmitting the notification over the network to the remote computing device further comprises:
   including in the transmission, executable code or a script that causes the remote computing device to prevent the particular individual from conducting the transaction.

16. A computer-implemented method for monitoring the containment of an epidemic in relation to a location-based restriction using an anonymized database of spending records, wherein the spending records concern purchases by respective individuals in a population at respective locations and at respective times, and wherein the database of spending records is updated in real time as the individuals conduct additional purchases, the method comprising:
   receiving, with a processor configured by instructions in the form of code executing therein, restriction data identifying a restricted location and a timeframe for the restriction;
   accessing, with the configured processor from the database of spending records, prior spending records that concern purchases conducted prior to the timeframe and current spending records that concern purchases conducted during the timeframe;
   determining, with the configured processor from the prior spending records, a historical transaction volume relating to the restriction;
   determining, with the configured processor from the current spending records, a current transaction volume relating to the restriction;

identifying, with the configured processor one or more transaction volume trends based on the current transaction volume and the historical transaction volume;

computing, with the configured processor, an effectiveness measure for the restriction based on the identified one or more transaction volume trends;

comparing the effectiveness measure to a prescribed target level;

based on the effectiveness measure not meeting the prescribed target level, transmitting, with the configured processor over a network to a remote computing device being used by a particular individual to perform a transaction in an area subject to the location-based restriction, a notification configured to cause the remote computing device to prompt the particular individual to perform at least one action at the remote computing device; and delaying, holding or declining the transaction, by the configured processor, pending receipt, by the configured processor, of an indication from the remote computing device that the least one action was performed by the particular individual at the remote computing device.

17. The method of claim 16, wherein the one or more transaction trends include one or more of:
an increase in transaction volume at the restricted location during the timeframe;
an increase in transaction volume at the restricted location for a subset of individuals in the population having a relation to the restricted location;
an increase in transaction volume for the subset of individuals at one or more alternative locations; and
a relative increase in transaction volume for particular products at the one or more alternative locations.

18. The method of claim 17, further comprising:
identifying, with the processor from the database of spending records, the subset of individuals having the relation to the restricted location, wherein the relation to the restricted location is one or more of:
a history of conducting transactions at the restricted location, and
a billing address that is proximate to the restricted location.

19. The method of claim 17, further comprising:
identifying, with the processor from the database of spending records, the particular products, wherein the particular products are one or more of:
products purchased at the restricted location, and
products that have a correlation to the epidemic;
identifying, with the processor from the database of spending records, the one or more alternative locations to purchase the particular products, wherein the one or more alternative locations are one or more of:
an online source for the particular products, and
an un-restricted location that is proximate to the restricted location.

20. The method of claim 16, wherein the one or more transaction trends are weighted according to a respective degree of correlation to the restriction.

21. The method of claim 16, further comprising:
generating, with the processor, a heat-map using one or more of:
the effectiveness measure, and
the one or more transaction trends,
wherein the notification representing the computed effectiveness measure includes the generated heat map or a link to retrieve the generated heat map.

22. The method of claim 1, wherein a spending record comprises transaction data including a location, a time of transaction, a merchant and one or more of: a product and a service.

23. The method of claim 1, further comprising: obtaining a permission from each of the individuals in the population to access respective spending records.

24. The method of claim 1, further comprising: anonymizing the spending records such that the individuals in the population are not personally identifiable from the spending records.

25. The method of claim 1, wherein each spending record is a transaction history from the use of a credit card, a debit card, a prepaid card, a gift card, bank account bill pay service or ACH payment or a combination of the foregoing.

26. A system for monitoring the containment of an epidemic in relation to a location-based restriction using an anonymized database of spending records, wherein the spending records concern purchases by respective individuals in a population at respective locations and at respective times, and wherein the database of spending records is updated in real time as the individuals conduct additional purchases, comprising:
a non-transitory computer-readable storage medium;
a processor configured by executing one or more software modules including instructions in the form of code stored in the storage medium, the modules including:
a database module, that configures the processor to access, from the database of spending records, prior spending records that concern purchases relating to a location of the location-based restriction and conducted prior to a timeframe of the location-based restriction and current spending records that concern purchases conducted during the timeframe;
an analysis module, that configures the processor to determine a historical transaction volume relating to the location from the prior spending records and a current transaction volume relating to the location from the current spending records, identify one or more transaction volume trends based on the current transaction volume and the historical transaction volume, compute an effectiveness measure for the restriction based on the identified one or more transaction volume trends; and
a reporting module that configures the processor to generate a notification if the computed effectiveness measure fails to meet a prescribed target level and transmit the notification to a remote computing device being used by a particular individual to perform a transaction in an area subject to the location-based restriction, wherein the notification wherein the notification is configured to cause the remote computing device to prompt the particular individual to perform at least one action at the remote computing device; and
an action processing module that configures the processor to delay, hold or decline the transaction pending receipt of confirmation from the remote computing device that the least one action was performed by the particular individual at the remote computing device.

* * * * *